United States Patent [19]

Nicol et al.

[11] 4,134,063

[45] Jan. 9, 1979

[54] APPARATUS FOR THE TIME-DEPENDENT MEASUREMENT OF PHYSICAL QUANTITIES

[76] Inventors: Klaus Nicol, Adelheidstr. 13,, 6000 Frankfurt; Ewald M. C. Hennig, Kirleweg 2a, 6454 Bruchköbel, both of Fed. Rep. of Germany

[21] Appl. No.: 700,905

[22] Filed: Jun. 29, 1976

[30] Foreign Application Priority Data

Jul. 2, 1975 [DE] Fed. Rep. of Germany ....... 2529475

[51] Int. Cl.² .......................................... G01R 27/26
[52] U.S. Cl. ................................................ 324/61 R
[58] Field of Search .................. 324/61 R, 60 C, 60 R, 324/140; 178/50; 179/175.2 R, 175.23; 328/130, 75; 239/63; 73/73

[56] References Cited

U.S. PATENT DOCUMENTS

| | | | |
|---|---|---|---|
| 3,363,064 | 1/1968 | Sperlich | 179/175.2 R |
| 3,392,333 | 7/1968 | Blondfield | 324/140 |
| 3,411,136 | 11/1968 | Ellis, Jr. et al. | 328/75 X |
| 3,492,446 | 1/1970 | Lapsevskis et al. | 179/175.2 R |
| 3,551,888 | 12/1970 | Balugani | 328/75 X |
| 3,688,190 | 8/1972 | Blum | 324/61 R |
| 3,725,614 | 4/1973 | Slana | 179/175.2 R |
| 3,760,115 | 9/1973 | Duerdoth et al. | 179/175.2 R X |
| 3,893,024 | 7/1975 | Reines et al. | 179/175.23 X |
| 3,991,375 | 11/1976 | Riggs et al. | 324/61 R X |

Primary Examiner—Stanley T. Krawczewicz
Assistant Examiner—Vincent J. Sunderdick
Attorney, Agent, or Firm—Bucknam and Archer

[57] ABSTRACT

An apparatus for measuring the values of physical parameters, using variable capacitor type transducers arranged in a matrix with each operable to sense the value of a corresponding physical parameter as existing at a predetermined point. A demultiplexer with input connected to a reference signal source and plural outputs each connected to a corresponding transducer electrically excites the transducers in sequence to aid said transducers in establishing respective output signals representing the value sensed. A multiplexer with plural inputs each connected to a corresponding transducer receives the output signals thereof, and the output of the multiplexer is connected to signal processing means which receives through the multiplexer in sequence the output signals of the transducers and recovers from such signals the parameter value information thereof.

4 Claims, 4 Drawing Figures

APPARATUS FOR THE TIME-DEPENDENT MEASUREMENT OF PHYSICAL QUANTITIES

BACKGROUND AND SUMMARY OF THE INVENTION

This invention relates in general to instruments and equipment for measuring the values of physical parameters to quantities.

In particular, the invention is directed to an apparatus which uses transducers, such as variable impedance electronic devices, to sense the parameter values at respective predetermined points. These transducer devices are expediently arranged in a matrix. A demultiplexer with an input connected to a reference signal source and plural outputs each connected to a corresponding transducer excites the transducers in sequence and thereby aids or activates the transducers to establish respective output signals each representing a value sensed. A multiplexer with plural inputs each connected to a corresponding transducer receives the output signals thereof, and the output of the multiplexer is connected to signal processing means which receives through the multiplexer in sequence the output signals of the transducers and recovers from such signals the parameter value information thereof.

The invention particularly concerns an apparatus for the time-dependent measurement of physical quantities and of the distribution of these quantities in space or in an area or along a line with an arrangement of at least four electronic devices whose output current is varied by the physical quantities.

In these known apparatus, either a separate electronic measuring system or a separate multiplexer channel is assigned to each electronic device. This has the disadvantage that the electronic expenditures become very high with a great number of structural elements.

The invention is based on the problem of providing an apparatus of the above mentioned type, where the number of multiplexer channels is clearly reduced relative to the number of structural elements.

This problem is solved in this way that a voltage generator is provided, which is connected to the input of a demultiplexer, of which each output is connected to a first terminal of at least two electronic devices, of which each has at least two terminals, that a current flows through the device over one of the other terminals when a voltage is applied to one terminal, which can be influenced by the physical quantity to be measured, that each input of a multiplexer is connected to the other terminals of at least two devices, and that a device for storing and/or processing and/or representing the signal carrying the information on the physical quantity is connected to the output of the multiplexer.

The apparatus has generally many electronic devices — usually bipolar devices or two-terminal networks-elements and therefore called hereafter "bipoles" — which are supplied with voltage over a demultiplexer and connected over a multiplexer to a processing device. The arrangement according to the invention makes it possible to measure physical quantities and their distribution in space, in an area or on a line in a simple manner.

The combination of the bipoles in the indicated manner in groups has the result that the number of channels of the multiplexer and demultiplexer is substantially below that of the bipoles.

If the bipoles have a complex resistance, or impedance, information on the physical quantity to be measured can be obtained, for example, over a simple voltage divider with a fixed resistance $R_k$, which can be arranged selectively before or after the multiplexer.

The distribution can be measured with sufficient accuracy by making the individual bipoles sufficiently small and arranging them close together.

If the bipoles have a matrix-form, for example, the terminals of one bipole can be combined in rows and be connected per row to a channel of the demultiplexer. The other terminals are combined in columns and can be connected to a measuring resistance (fixed resistance $R_k$) and to a channel of the demultiplexer. This way a × b bipoles can be supplied by a + b channels.

Any bipole can thus be clearly identified by indicating the single demultiplexer and the single multiplexer channel associated with the bipole.

If alternating current flows over the terminals combined in columns, it is of particular advantage if a rectifying, filtering and amplifying device is arranged between these terminals of the bipoles and the inputs of the multiplexer to the measuring resistance, and if this device is arranged directly next to the bipoles to eliminate the interfering influences of the line-capacitances.

There is a possibility that the current will flow to the multiplexer not only over the bipole that has just been connected, but also over a chain of parallel-connected bipoles. If all output lines of the demultiplexer are loaded each with an ohmic resistance $R_i$, whose value is relatively small, this interfering influence is eliminated.

The determination of the distribution of special physical quantities in space is possible, since the electronic devices are designed as structural elements whose current is influenced in a defined manner by the physical quantities to be measured over the terminal connected to the multiplexer.

For example, the bipoles can be designed as sensors for the spatial distribution of

- section lengths where spatial arrangements vary the size of a resistance value, a capacitance, or an inductance (used, e.g. in scanning surfaces)
- pressure, where the pressure varies the size of a resistance value, a capacitance or an inductance. In particular gas pressure (sound pressure-) distribution can be measured with microphone arrangements or the distribution of the pressure under uneven or soft bodies with arrangements of capacitors with a compressible dielectric or with arrangements of pressure-sensitive resistance material,
- temperature on the basis of temperature-sensitive resistances
- light on the basis of photo-resistances or photo-diodes
- electromagnetic fields on the basis of induction loops or Hall generators.
- X-ray, gamma or corpuscular radiation by using corresponding bipoles networks.

One embodiment of the invention serves in particular to measure forces and distribution of forces exerted by the human body on a support.

The movement of the human body in time and space — one of the central tasks of biology, medicine, works science and sports science — is described by indicating:

(a) the locomotion of body and body parts and
(b) the forces which effect this locomotion.

Locomotions can be observed visually and can be recorded simply by means of photography but the forces which effect these locomotions can not be observed directly, while the presently known dynamometers are relatively ineffective and to elaborate for biological objects.

The most common constructions for determining the forces acting upon a large area on a force-absorbing surface of a measuring transducer are the so-called "biochemical measuring platforms," where the forces are exerted on metal plates and transmitted from there mostly over four force-transducers, on a strain gauge or piezo gauges to a bottom plate. These measuring platforms are relatively heavy and extend several centimeter in height, so that they must be buried into the ground for many application. They are rigid and measure only the total force, but not its areal distribution.

An apparatus is already known (German Offenlegungsschirft No. 2,345,551) where a pressure-sensitive capacitor arrangement with a compressible dielectric is used for the determination of mechanical quantities on biological objects. The pressure-sensitive capacitor-arrangement is designed as a single channel mat, by means of which the activity of babies is monitored. An examination of the mode of operation of this apparatus by the applicant shows that the signals obtained here are derived first from the variation of the total force originating from the acceleration of body parts, and second from the variation of the pressure distribution with a constant total force. A disadvantage of this arrangement is that, because of the mixing of these effects, it is only possible to obtain qualitative data on "activites", but not quantitative data on the force and pressure distribution over the surface of the mat. The known apparatus is thus not suitable for exact force measurements proper.

The invention provides an apparatus which permits not only to measure forces accurately, but also to determine the force distribution reliably and in a simple manner.

To this end the electronic devices in the arrangement according to claim 1 are designed as pressure-sensitive capacitors, with an easily compressible non-conductor as a dielectric arranged between the capacitor plates, whose geometry and dielectric are so selected that the dielectricity constant divided by the plate distance is proportional to the force to be measured, the evaluating and indicating means can then be very simple, since the capacitance of a capacitor varies linearly to the force and is independent of the force distribution over the (flexible) plate surface.

With a flexible design of the dielectric and of the capacitor plates we obtain an arrangement which permits to measure forces and force distributions in a simple manner, even when the measurement is to be made on an uneven and soft ground.

In a practical embodiment, the capacitors of the circuit form each a member of an a-c fed R-C voltage divider so that the voltage tapped on the resistance indicates the force, after rectification and filtering. This arrangement permits to use a great number of capacitors for measuring forces without a great engineering effort. Since the capacitors can be in addition very small, it is possible this way to determine force distributions with a high area resolution.

The mechanical design can be simplified particularly by using, pressure-sensitive capacitors which are formed on a mat of natural rubber, the front and back of the mat being pasted with parallel strips of metallized plastic, the directions of the strips on the two sides being so selected that the parallel strips of one side cross and overlap those of the other side. The use of natural rubber as a dielectric ensures adherence to the equation $\epsilon/d = a.K + b$. Due to this arrangement it is possible in a simple manner to measure the distribution of forces acting perpendicularly on a surface, particularly when the measurement is to be made on uneven and soft ground. The transducer is particularly light and flexible in this embodiment, and has a low overall height, so that it can be used for many purposes.

As mentioned above, in an arrangement operated with alternating current, there is a possibility that the alternating current will flow to the multiplexer not only over the measuring capacitor that has just been connected, but also over a chain of parallel-connected capacitors. If the output lines of the demultiplexer are loaded each with an ohmic resistance whose value is low compared to the apparent resistance of a measuring capacitor at the frequency of the measuring voltage, this interfering influence is reduced to an acceptable level.

The measuring resistance and the rectifier are preferably arranged directly on the mat, otherwise the capacitance of the feed cable exceeds that of the capacitors by a multiple, which leads to considerable disturbances.

For a better understanding of the invention and its various advantages, reference should be had to the following detailed description and accompanying drawings which together exemplify a preferred embodiment of the invention.

DESCRIPTION OF A PREFERRED EMBODIMENT OF THE INVENTION

Figure 1:
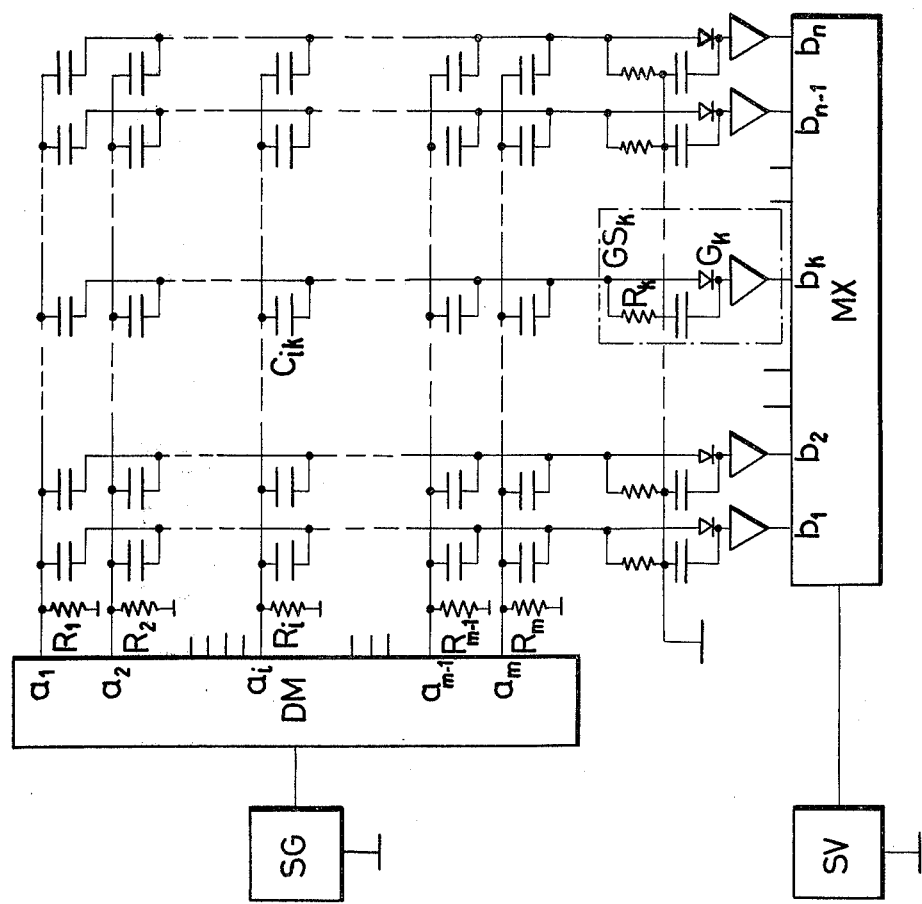
FIG. 1 is a schematic circuit and block diagram of a measuring apparatus according to a preferred embodiment of the invention which uses a matrix arrangement of capacitor type transducers.

In FIG. 1 there is illustrated an apparatus for measuring the values of physical parameters by using a plurality of capacitors designated each generally as Cik, and which are actually transducers in the form of variable capacitors. Each capacitor transducer Cik is operable to sense the value of a corresponding physical parameter to be measured, as for example by connecting or arranging the plates of the capacitor so that they move in accordance with the value of the parameter under measurement.

In the apparatus according to FIG. 1, a demulitplexer DM is fed from an AC voltage generator SG. The outputs of the demultiplexer DM, which are designated with $a_1, a_2, \ldots, a_i, a_{m-1}, a_m$, are connected in rows to the respective terminals of a matrix-type arrangement of capacitors Cik, which have two capacitor plates. Furthermore an ohmic resistance $R_1, R_2 - - - R_m$ is connected to each output $a_1 - - - a_m$. One set of terminals of the capacitors Cik, which are each connected to one of the capacitor plates thereof, are combined in columns with devices $GS_k$ for rectification filtering and amplification. Each column line is in turn grounded over a second resistance Rk of a voltage divider in devices GSk. The outputs of the devices GSk are connected to the inputs $b_1$, $b_2$ -- $b_k$ --- $b_{n-1}$, $b_n$ of a multiplexer MX. The output of the multiplexer is connected to a device SV for storage, processing and representation.

The capacitors Cik are scanned successively by means of the demultiplexer DM and of the multiplexer MX, and the flowing current is transmitted, for example, by a certain brightness value to a display unit. If the degree of action of the force to be measured on one or several capacitors varies, the brightness in the display unit will vary correspondingly for the respective panel.

With an adequate fine division of the measured value-pickup, it is possible to represent distributions with a high resolution.

On the other hand, force and time can be represented on a multiple diagram.

Figure 2:
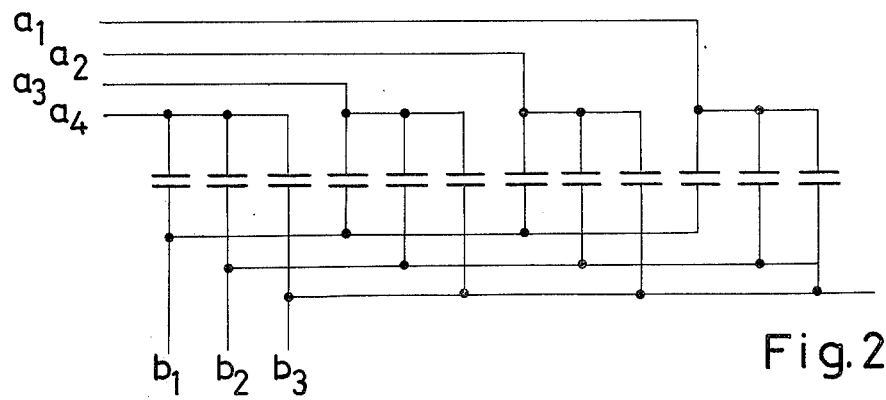
FIG. 2 is a schematic circuit diagram of a matrix of capacitor type transducers which could be used in the apparatus of FIG. 1 in place of the larger capacitor matrix shown therein.

FIG. 2 shows a capacitor arrangement expediently in rows, where individual capacitors are combined to groups with the common terminals $a_1$ to $a_4$. The capacitor plate of the capacitors of each group is connected to one output each of the demultiplexer, while the other plate of the n-th capacitor of each group is connected to an input $b_1$ to $b_3$ of the multiplexer. The circuit works principally exactly like the circuit represented in FIG. 1. In this arrangement too, the capacitors can be scanned with simple means.

Figure 3:
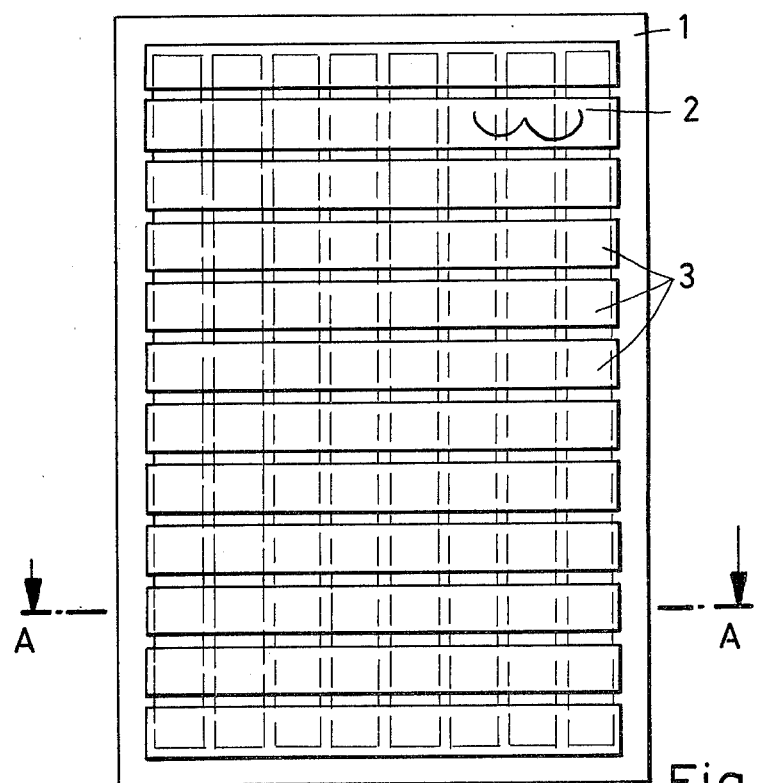
FIG. 3 is a schematic plan view of a capacitor transducer matrix that can be used in the apparatus of FIG. 1, and which uses a resilient dielectric mat upon which metallic strips are arranged to form the capacitors.
Figure 4:
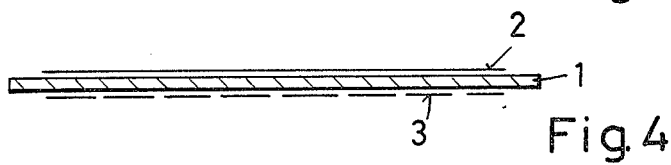
FIG. 4 is a sectional view of the capacitor transducer matrix shown in FIG. 3 as taken along line A—A therein.

FIG. 3 shows a mat 1 with metallized plastic strips 2 on the front and with metallized plastic strips 3 on the back, which are represented in broken lines. The mat is shown again for clarity's sake in a section in FIG. 4, the strip on the front of the mat being cut in its longitudinal direction, while the strips on the back of the mat are cut in its transverse direction.

From the foregoing description, it will be appreciated by the artisan that the invention utilizes a basically simple concept to achieve measurement of a multiplicity of variables, or the same basic variable at a multiplicity of distribution points, with a savings in equipment as compared to prior art measurement techniques.

Each of the transducers exemplified in FIG. 1, while shown to be a variable capacitor type device, could be any other variable impedance device, particularly when the reference signal source SG puts through the demultiplexer DM an AC excitation voltage. It should be noted that the demultiplexer is merely a cyclically repeatable single pole multiposition switch that is driven either mechanically or electronically so that the imput terminal is connected to each output terminal, one at a time in sequence. Conversely, the multiplexer is the same type of cyclical stepping switch as is the demultiplexer, except that the connections are reversed so that a plurality of inputs are connected one at a time in sequence to a single output. The reference signal source thus is connected so that all of the capacitors associated with a given row are energized with an AC voltage at the same time. Thus, when the demultiplexer switching state results in connection of the output $a_i$ to the signal generator SG, one set of plates or terminals of all capacitors Cik in the i-th row will be connected at the same time to the alternating voltage signal source. However, the other terminals of the capacitors in the i-th row are connected through the recitification filtering and amplifying units GS to inputs of the multiplexer, and only one input at a time of the multiplexer is connected to the output thereof for information recovery by the signal processing means SV. Thus, at any given time a single excited capacitor is deliverying an information signal, when the demultiplexer excites the i-th row and the multiplexer connection is through the k-th column the capacitor Cik will be energized. This capacitor Cik is connected in series to ground through the resistance $R_k$ such that the alternating voltage applied to the input of the device $GS_k$ will depend upon the voltage drop or attenuation through capacitor $C_{ik}$.

While the capacitance of any given capacitor $C_{ik}$ and hence its impedance, will vary with the value of the variable it senses, because at each instant an entire row of capacitors is connected to the reference signal source SG, the invention provides means to minimize to an acceptable level the amount of interference signal fed to the active multiplexer input by reason of current flow paths through a series of adjacent other capacitors in the matrix. This is done by providing resistors $R_1$, $R_2$, $R_i$---, $R_{m-1}$, $R_m$ connected each from a respective output of the demultiplexer to ground. The resistance value of these resistors $R_1$ - - - $R_m$ is small as compared to the impedance of the capacitors $C_{ik}$, but high as compared to the impedance of the device SG as seen at the demultiplexer outputs.

It should furthermore be noted by the artisan that while the capacitors Cik are shown electrically connected in a rectangular matrix having a number of rows determined by the number of outputs of the demultiplexer and a number of columns determined by the number of inputs of the demultiplexer, such arrangement of transducer devices merely gives an orderly scanning sequence. The physical placement of the transducers, whether they be capacitor type or otherwise, need not be in all cases in a physical rectangular matrix arrangement, as is exemplified by the capacitor matrix mat structure of FIGS. 3 and 4.

What is claimed is:

1. Apparatus for measuring the values of physical parameters, which comprises a plurality of transducers each operable to sense the value of a corresponding physical parameter to be measured and to establish, when excited, an electrical analog output signal representing the parameter value sensed; a demultiplexer having an input connected to a reference signal source and a plurality of outputs each connected to at least one corresponding transducer to connect same with said source to thereby electrically excite same by said source in sequence to thereby establish the respective output signals of said transducers; a multiplexer having a plurality of inputs each connected to at least one corresponding transducer to receive the output signal thereof, and an output; signal processing means connected to the output of said multiplexer to receive therethrough in sequence the output signals of said transducers and to recover from such signals the parameter value information thereof, said transducers being variable impedance devices in which the impedance varies in accordance with the value of the parameter sensed, and said reference signal source is an alternating voltage source whereby said transducer analog output signals are respective alternating voltages with amplitudes dependent upon the value of the parameter sensed.

2. Apparatus according to claim 1 wherein said plurality of transducers include a corresponding plurality of independently variable capacitors electrically interconnected in a matrix with the capacitors associated with each row of the matrix being connected to a respective common node and the capacitors associated with each column of the matrix being connected to another respective common node.

3. Apparatus according to claim 2 wherein said matrix of capacitors is defined by a plurality of parallel metallic strips positioned against respective opposite sides of a sheet of resilient dielectric material.

4. Apparatus according to claim 1 including a plurality of resistors each electrically connected between a ground element and a corresponding output of the demultiplexer, the resistance value of said resistors being low in comparison to the impedance of a transducer at the frequency of said reference signal source.

* * * * *